(12) United States Patent
Gower et al.

(10) Patent No.: US 10,092,508 B2
(45) Date of Patent: Oct. 9, 2018

(54) POLYMER IMPLANTS FOR TREATMENT OF METABOLIC DISORDERS

(71) Applicant: UNIVERSITY OF SOUTH CAROLINA, Columbia, SC (US)

(72) Inventors: Robert Gower, Columbia, SC (US); Michael Hendley, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/634,093

(22) Filed: Jun. 27, 2017

(65) Prior Publication Data
US 2017/0367974 A1    Dec. 28, 2017

Related U.S. Application Data

(63) Continuation of application No. 62/355,486, filed on Jun. 28, 2016.

(51) Int. Cl.
| | | |
|---|---|---|
| *A61K 9/24* | (2006.01) | |
| *A61K 9/00* | (2006.01) | |
| *A61K 9/50* | (2006.01) | |
| *A61K 31/05* | (2006.01) | |

(52) U.S. Cl.
CPC .......... *A61K 9/0024* (2013.01); *A61K 9/5031* (2013.01); *A61K 31/05* (2013.01)

(58) Field of Classification Search
CPC .................................................. A61K 9/0024
USPC ....................................................... 514/730
See application file for complete search history.

(56) References Cited

U.S. PATENT DOCUMENTS

| | | | |
|---|---|---|---|
| 6,569,633 B1 | 5/2003 | Wilkison et al. | |
| 8,992,471 B2 * | 3/2015 | Dugas ...................... | A61L 31/10 604/103.02 |
| 2003/0022856 A1 | 1/2003 | Richardson et al. | |
| 2014/0162996 A1 | 6/2014 | Rahbar et al. | |

OTHER PUBLICATIONS

Wang, Expert Rev Endocrinol Metab. 2015; 10(6): 561-564.*
Hollinger, Journal of Biomedical Materials Research, vol. 17,71-82 (1983).*
Richardson, Thomas P., William L. Murphy, and David J. Mooney. "Selective adipose tissue ablation by localized, sustained drug delivery." Plastic and reconstructive surgery 112.1 (2003): 162-170.
Szkudelski, Tomasz, and Katarzyna Szkudelska. "Anti-diabetic effects of resveratrol." Annals of the New York Academy of Sciences 1215.1 (2011): 34-39.
Ogden, Cynthia L., et al. "Prevalence of childhood and adult obesity in the United States, 2011-2012." Jama 311.8 (2014): 806-814.
Kahn, Barbara B., and Jeffrey S. Flier. "Obesity and insulin resistance." Journal of clinical investigation 106.4 (2000): 473.
Kershaw, Erin E., and Jeffrey S. Flier. "Adipose tissue as an endocrine organ." The Journal of Clinical Endocrinology & Metabolism 89.6 (2004): 2548-2556.
Timmers, Silvie, et al. "Calorie restriction-like effects of 30 days of resveratrol supplementation on energy metabolism and metabolic profile in obese humans" Cell metabolism 14.5 (2011): 612-622.
Price, Nathan L., et al. "SIRT1 is required for AMPK activation and the beneficial effects of resveratrol on mitochondrial function." Cell metabolism 15.5 (2012): 675-690.
Lagouge, Marie, et al. "Resveratrol improves mitochondrial function and protects against metabolic disease by activating SIRT1 and PGC-1α." Cell 127.6 (2006): 1109-1122.
Baur, Joseph A., and David A. Sinclair. "Therapeutic potential of resveratrol: the in vivo evidence." Nature reviews Drug discovery 5.6 (2006): 493-506.
Finkelstein, Eric A., et al. "Annual medical spending attributable to obesity: payer-and service-specific estimates." Health affairs 28.5 (2009): w822-w831.
Gower, R. Michael, et al. "Modulation of leukocyte infiltration and phenotype in microporous tissue engineering scaffolds via vector induced IL-10 expression" Biomaterials 35.6 (2014): 2024-2031.
Liu, Jeffrey MH, et al. "Transforming growth factor-beta 1 delivery from microporous scaffolds decreases inflammation post-implant and enhances function of transplanted islets." Biomaterials 80 (2016): 11-19.
Graham, John G., et al. "PLG scaffold delivered antigen-specific regulatory T cells induce systemic tolerance in autoimmune diabetes." Tissue Engineering Part A 19.11-12 (2013): 1465-1475.
Grozinger, Christina M., et al. "Identification of a class of small molecule inhibitors of the sirtuin family of NAD-dependent deacetylases by phenotypic screening." Journal of Biological Chemistry 276.42 (2001): 38837-38843.

* cited by examiner

*Primary Examiner* — Nizal S Chandrakumar
(74) *Attorney, Agent, or Firm* — Dority & Manning, P.A.

(57) ABSTRACT

Implantable devices including a biocompatible matrix configured for long term location in adipose tissue and a biologically active agent that can be carried by the matrix and delivered to the adipose tissue following implant therein. The biologically active agent can include a modulator or a precursor thereof that can directly or indirectly modify the gene expression of adipose cells, e.g., adipocytes, and thereby modify the presence or quantity of one or more expression products of the adipose tissue that may act locally on distant from the implant site in an endocrine fashion. Modulators can include small molecules (e.g., resveratrol), polynucleotides (e.g., RNAi), or polypeptides (e.g., antibodies or functional fragments thereof).

5 Claims, 15 Drawing Sheets

POLYMER IMPLANTS FOR TREATMENT OF METABOLIC DISORDERS

CROSS-REFERENCE TO RELATED APPLICATION

This application claims filing benefit of U.S. Provisional Patent Application Ser. No. 62/355,486 having a filing date of Jun. 28, 2016 entitled "Drug Releasing Polymer Implants for the Treatment of Metabolic Disorders," which is incorporated herein by reference for all purposes.

STATEMENT REGARDING FEDERALLY SPONSORED RESEARCH OR DEVELOPMENT

This invention was made with government support under grant 5 P20 GM103641 05 awarded by National Institutes of Health. The government has certain rights in the invention.

BACKGROUND

Obesity is a major risk factor for heart disease, stroke, type 2 diabetes, and certain types of cancer as well as other pathologies. The current therapies for obesity focus on lifestyle changes and include eating fewer calories and increasing physical activity, with medications and highly invasive weight loss surgery being options if lifestyle changes are ineffective. Unfortunately, despite widespread implementation of these therapies there has been no significant decrease in the prevalence of obesity within the U.S. over the past decade. More recent approaches have suggested that in order to increase success rates in treatment for obesity it may be necessary to focus more attention on underlying metabolic disorders for which obesity may be a symptom, rather than a cause.

Metabolic syndrome is a term used to identify individuals exhibiting at least three of five medical conditions including abdominal (central) obesity, elevated blood pressure, elevated fasting plasma glucose, high serum triglycerides, and low high-density lipoprotein (HDL) levels. When obesity is found in combination with two or more of these other conditions in metabolic syndrome, the risk of developing life threatening disease such as cardiovascular disease and type 2 diabetes becomes even greater. It is estimated that in the USA, about a quarter of the adult population have metabolic syndrome, and the prevalence increases with age, with racial ethnic minorities being particularly affected.

The interrelationship of obesity with metabolic syndrome leading to type 2 diabetes and cardiovascular disorders ranks among the most important health problems facing Western and Westernized populations. Clinical abnormalities in these disorders, including hyper/dyslipidemia, insulin resistance, and glucose intolerance are each independent cardiovascular risk factors that are usually treated piecemeal and with limited success.

What are needed in the art are materials and methods for treating metabolic disorders, and in particular those leading to obesity. Materials and methods capable of treating the underlying causes of metabolic syndrome and in particular obesity would be of great benefit.

SUMMARY

According to one embodiment, disclosed is a method for treating metabolic disorders. A method can include implanting a biocompatible structure in adipose tissue. The biocompatible structure can include a biocompatible matrix and a biologically active agent encapsulated within, bonded to, or as a component of the biocompatible matrix. The biologically active agent can include an adipose tissue expression product modulator (also referred to as a "modulator" herein) or a precursor thereof, i.e., a compound that can function as a direct or indirect modulator (e.g., an expression or activity modulator) of one or more components of the secretome of the adipose tissue in which the biologically active agent is implanted. The modulator can have an effect that is local and/or distant to the implant site. The method can be utilized in one embodiment to treat a metabolic disorder that can lead to one or more symptoms of metabolic syndrome, such as one or more of obesity, hyperglycemia, HDL levels, etc.

Also disclosed is a biocompatible implant configured for long term (e.g., days, weeks, months) location in adipose tissue. The biocompatible implant can include a biocompatible matrix and a biologically active agent encapsulated within, bonded to, or a component of the biocompatible matrix. The biologically active agent can include an adipose tissue expression product modulator or a precursor thereof. In one embodiment, the biocompatible matrix can be degradable and/or can be configured to release the biologically active agent at a sustained release rate over time.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
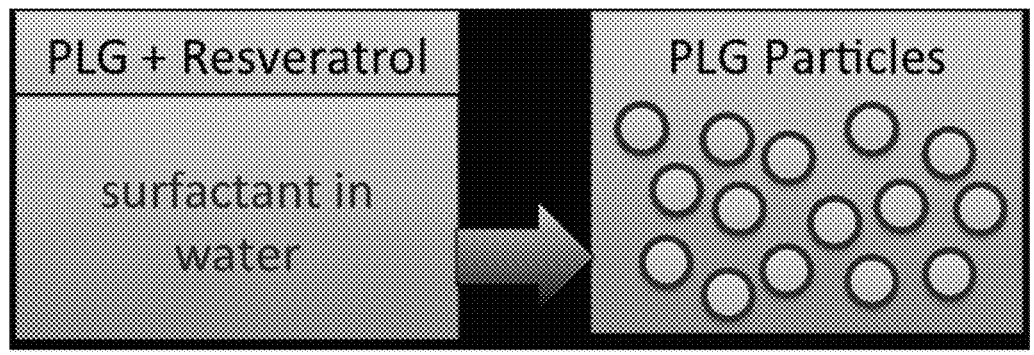
FIG. 1 schematically illustrates an emulsion technique as may be utilized in forming an implant.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to methods and materials for treatment of metabolic disorders. More specifically, disclosed are methods and materials that can be beneficially utilized for treatment of one or more medical conditions recognized as components of metabolic syndrome e.g., obesity, hyperglycemia, LDL levels, serum triglyceride levels, etc. as well as other conditions related to disorder of the metabolic system including, without limitation, type 2 diabetes, pre-diabetes, cardiovascular disease, etc. Disclosed methods focus on treatment of metabolic disorders underlying health-threatening conditions such as obesity, diabetes, cardiovascular disease, etc. through modification of gene expression in the adipose tissue, a major energy regulating organ. Disclosed methods can be utilized to modify gene expression of one or more components of adipose tissue including, and without limitation to, adipocytes, progenitor cells, immune cells, and vascular cells. All of the cell types of adipose tissue can have a role in metabolic disease, and disclosed methods and materials can be tailored to affect the expression products of one or more of these cell types in treatment of metabolic disorders. For instance, adipocytes can regulate energy homeostasis by storing excess energy as lipids and by releasing molecules that can modulate metabolism both locally and in distant organs in an endocrine-like fashion. Immune cells present in adipose tissue can express endocrine factors that can likewise modulate metabolism both locally and in distant organs.

The lipid stores and secretome of adipose tissue cells are intimately linked; for example, large lipid stores lead to the secretion of factors that promote insulin resistance and metabolic disease. As such, through modification of the secretome of cells of adipose tissue, e.g., adipocytes, disclosed methods can also modify the lipid storage characteristics of adipose tissue in treatment of characteristics associated with metabolic syndrome including obesity, high blood pressure, poor glucose metabolism, high triglyceride levels, cholesterol levels, etc. for use in treatment or prevention of related pathologies (cardiovascular disease, type 2 diabetes, etc.).

Implantable devices include a biocompatible matrix (also referred to herein as a scaffold) configured for long term location in adipose tissue and a biologically active agent that can be carried by the matrix and delivered to the adipose tissue following implant therein. The biologically active agent can include an adipose tissue expression product modulator or a precursor thereof. As utilized herein, the term "adipose tissue expression product modulator" is intended to refer to a compound that can directly or indirectly modify the gene expression or activity of adipose tissue cells and thereby modify the presence, activity, or quantity of one or more expression products of the cells. The term "precursor" generally refers to a compound that can be modified following implantation to provide or otherwise encourage formation of a modulator. For example, an adipocyte modulator precursor can be a construct or a polymer or other molecule that upon hydrolysis, in vivo enzymatic activity, or some other modification process, can form or release an adipocyte modulator. In one embodiment, a modulator precursor can include an expression cassette that can be configured to express a modulator (or a precursor thereof, e.g., an siRNA precursor) following implantation in adipose tissue.

Modulators can modify the expression of one or more genes through either increase or decrease of expression. In addition, modulators can modify the expression of genes, the expression product of which carry out one or multiple functions near the implantation site, e.g., within the adipose tissue, and/or external to the adipose tissue in which the implant is located. By way of example and without limitation, when considering local effects, modulators can directly or indirectly modify one or more of cell growth and/or differentiation, catecholamine responsiveness, triglyceride synthesis, lipase activity, differentiation-specific gene expression, lipid metabolism (e.g., lipogenesis and/or lipolysis), fatty acid uptake, and accumulation of cytoplasmic lipid.

A modulator can be in any suitable form, including and without limitation to a small molecule (e.g., having a number average molecular weight of about 1000 Da or less), a polypeptide (e.g., a protein, an antibody, or a functional fragment thereof, an enzyme, etc.), a polynucleic acid (e.g., a DNA or RNA construct (e.g., an expression cassette), a ribozyme, etc.), and can directly or indirectly decrease or increase the expression of one or more genes of one or more cell types of adipose tissue. For example, an indirect activity can be one in which a modulator modifies the expression of a gene, the expression product of which can in turn modulate, e.g., decrease, expression of a polypeptide either within or external to the adipose tissue. That polypeptide can likewise affect (e.g., inhibit) a target that can be either within or external to the adipose tissue.

In one embodiment, a modulator can include nucleotide-based materials such as RNA interference (e.g., dsRNAi or siRNA), antisense RNA, ribozymes, and triple helices. For example, RNA that is complementary to a targeted nucleic acid can silence protein expression of the targeted gene. A dsRNA can generally include a region that is complementary to a coding region of the nucleic acid, e.g., a 5' coding region, a region encoding a core domain, a 3' coding region, or a non-coding region, e.g., a 5' or 3' untranslated region.

A modulator can be or can encourage expression of an antibody or functional fragment thereof. For example, immunoglobulins can be implanted or produced that bind to an expression product or a binding partner thereof (e.g., a transcription factor) and thereby modify the adipose secretome. For example, an adipocyte modulator (or an expression product thereof) can bind to a protein and prevent enzymatic activity thereof or an interaction between a protein and its binding partner. In one embodiment, an immunoglobulin can be human, humanized, deimmunized, or otherwise non-antigenic in a subject.

In one embodiment, a modulator can modulate the expression of a sirtuin, the expression of which has been linked to a variety of metabolic disorders. Sirtuins are mammalian homologs of SIR2 proteins and are a homologous family of proteins. The SIR2 gene family has diverse functions in yeast including gene silencing, DNA repair, cell-cycle progression, and chromosome fidelity in meiosis and aging. Many of these proteins can function as NAD-dependent protein deacetylases. In one embodiment, a modulator can be an SIRT1 regulator, e.g., an SIRT1 inhibitor or activator. SIRT1 is the expression product of the gene hSIR2 and is the human homolog of the S. cerevisiae Sir2 protein known to be involved in cell aging. Human SIRT1 mRNA is disclosed at GenBank Accession No. AF083106. SIRT1 is a recognized regulator of adipocyte physiology.

In one embodiment, a modulator can be an SIRT1 activator, and in one particular embodiment can be a polyphenolic SIRT1 activator. Polyphenolic compounds encompassed can include, without limitation, those described by the following structure:

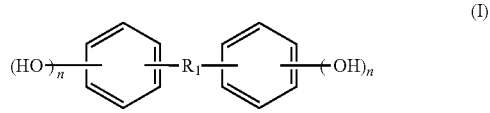
(I)

in which $R_1$ is alkenyl, C(O)CH=CH, or a hydroxy pyranone fused to one of the phenyl moieties to form a flavone; and each n is independently 1-3.

For example, a modulator can be a polyhydroxy stilbene (e.g., polyhydroxy-trans-stilbene) as shown in formula (II), a polyhydroxy chalcone as shown in formula (III), or a polyhydroxyflavone as shown in formula (IV). In one embodiment, the modulator can be substituted with at least 2, e.g., 3, 4, or 5 hydroxy moieties.

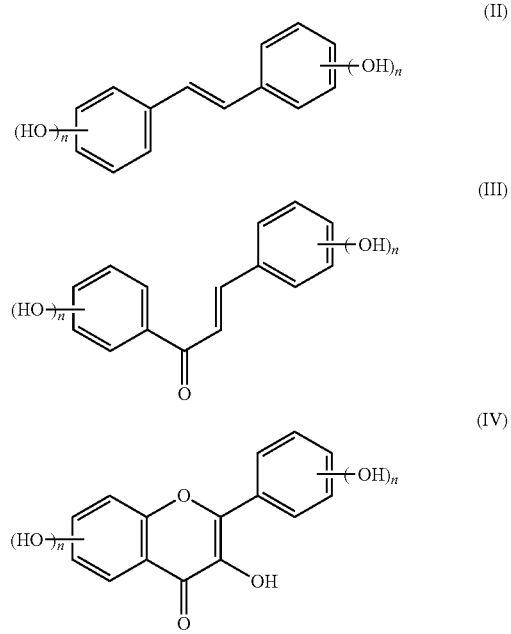

Exemplary modulators of this type can include, without limitation, resveratrol (3,5,4'-trihydroxy-trans-stilbene), butein (3,4,2',4'-tetrahydroxychalcone); piceatannol (3,5,3', 4'-tetrahydroxy-trans-stilbene); isoliquiritigenin (4,2',4'-trihydroxychalcone); fisetin (3,7,3',4'-tetrahydroxyflavone); and quercetin (3,5,7,3',4'-pentahydroxyflavone).

Resveratrol has emerged as a promising therapeutic for obesity because it mimics effects seen with calorie restriction including decreasing adipose lipid stores. While oral administration of polyphenolic compounds such as resveratrol in animal models has been shown to prevent weight gain and insulin resistance associated with a high fat diet, treatments have poorly translated in humans, in part due to the low bioavailability inherent in oral administration.

Exemplary inhibitors of SIRT1 activity include, and without limitation, Compound A3 (8,9-dihydroxy-6H-(1)benzo-furo[3,2-c]chromen-6-one), Compounds M15 (1-[(4-methoxy-2-nitro-phenylimino)-methyl]-naphthalene-2-ol) and Sirtinol (2-[(2-hydroxy-naphthalen-1-ylmethylene)-amino]-N-(1-phenyl-ethyl)-benzamide). Such compounds are available, e.g., from ChemBridge, or can be synthesized. See, e.g., Grozinger, et al. (J Biol Chem. 2001 Oct. 19; 276(42):38837-43. Epub 2001 Aug. 1)-Identification of a class of small molecule inhibitors of the sirtuin family of NAD-dependent deacetylases by phenotypic screening. Other examples of modulators as may be incorporated in a device can include derivatives of aryl and heterocyclic ureido aryl and heterocyclic carboxamido isobutyric acids, dichlorophenyl urea, curcumin, and 1,3-diazetidine-2,4-dione.

Examples of derivatives of aryl and heterocyclic ureido aryl and heterocyclic carboxamido isobutyric acids include, without limitation, [4-[(3,5-dichlorophenylureido)phenoxy-isobutyril]-4-aminobenzoic acid], [4-(3,5-dichlorophenylu-reido)phenoxyisobutyryl-1-amidocyclohexane-1carboxylic acid], and [1-(4-chlorobenzyl)-3-dichlorophenylureido)-4-phenoxyisobutyric acid].

Examples of derivatives of dichlorophenyl urea include, without limitation, [1,3-bis(3,4-dichlorophenyl)urea], [1,3-bis(3,5-dichlorophenyl)urea], [1-(3,5-dichlorophenyl)-3-(4- carboxyphenyl)urea], [1-(3,5-dichlorophenyl)-3-(4-methoxy-[1,1'-bisphenyl]-3-yl)urea], [1-(3,5-dichlorophenyl)-3-(3-chloro-4-hydroxyphenyl)urea], [1-(3,5-dichlorophenyl)-3-(3,5-dichloro-2-hydroxy-4-methyphenyl)urea], [1-(3,5-dichlorophenyl)-3-(3,5-dichloro-2-hydroxyphenyl)urea], [1-(3,5-dichlorophenyl)-3-(3,4,5-trichlorophenyl)urea], [1,3-bis(3,4,5-trichlorophenyl)-3-(2,3,5-trichlorophenyl)urea], [1-(3,5-dichloro-4-methylphenyl)-3-(3,5-dichlorophenyl)urea], [1-(2,6-dichloropyridin-4-yl)-3-(3,5-dichlorophenyl)urea], and [1-(2-chloropyrimidin-4-yl)-3-(3,5-dichlorophenyl)urea].

Examples of curcumin derivatives include, without limitation, [1,7-bis(4'-acetoxy-3'-methoxyphenyl)-3,5-heptadione] and [(1E,4Z,6E)-7-(4''-acetoxy-3''-methoxyphenyl)-5-hydroxy-1-(4'-hydroxy-3'-methoxyphenyl)hepta-1,4,6-trien-3-one].

An example of a 1,3-diazetidine-2,4-dione derivative includes, without limitation, [1,3-bis(3,5-dichloro-2-hydroxyphenyl) 1,3-diazetidine-2,4-dione].

Additional examples of modulators encompassed herein can include, without limitation to, medications such as metformin or glipizide (or combinations thereof such as Metaglip™), metabolites such as lactic acid (which can also be delivered as a breakdown product of the matrix, as discussed further herein), growth factors, and so forth.

In accord with the disclosure, one or more biologically active agents that can include one or more modulators or precursors thereof can be incorporated in conjunction with a biocompatible matrix for implant into adipose tissue. In general, any bulk biocompatible material capable of being formed to a useful size for implant in adipose tissue can be utilized in forming the devices. In one embodiment, a polymeric material can be utilized. For instance, a biocompatible matrix formed from polystyrene, poly(lactic acid), polyketal, butadiene styrene, styrene-acrylic-vinyl terpolymer, poly(methyl methacrylate), poly(ethyl methacrylate), poly(alkyl cyanoacrylate), styrene-maleic anhydride copolymer, poly(vinyl acetate), poly(vinyl pyridine), poly(divinylbenzene), poly(butylene terephthalate), acrylonitrile, vinyl chloride-acrylates, poly(ethylene glycol), and the like, or an aldehyde, carboxyl, amino, hydroxyl, or hydrazide derivative thereof can be utilized. Biocompatible scaffolds formed of biological polymers such as proteins can be used in one embodiment. For instance, a matrix formed of albumin, dextran, gelatin, chitosan, etc. can be utilized. Such materials can be preferred in certain embodiments as they can be formed without the use of organic solvents according to known methods.

Other inorganic biocompatible materials as may be utilized in forming an implantable device can include, without limitation, oxides such as silica, titania, zirconia, and the like, and noble metals such as gold, silver, platinum, palladium, and the like. In general, the materials will be biocompatible and nonimmunogenic.

In one embodiment, the matrix can be biodegradable. For instance, biodegradable polymeric materials formed from polysaccharide and/or poly(lactic acid) homopolymers and copolymers can be used. For example, a biocompatible matrix formed of poly(lactide-co-glycolide) (PLG) copolymers and derivatives thereof can be utilized. In another embodiment a poly(ethylene glycol) (PEG)/poly(lactic acid) (PLA) block copolymer can be utilized in forming a biocompatible matrix. A biodegradable lactic acid-based polymer matrix may be beneficial in one embodiment, as the degradation process can release lactic acid into the adipose tissue. Lactic acid has been suggested as an adipocyte modulator and as such, in this embodiment, the matrix degradation product lactic acid can be provided to the adipose tissue as a modulator, optionally in conjunction with one or more additional biologically active agents (e.g., additional modulators).

Many factors can be considered in designing and forming the biocompatible matrix that may be used to influence release of a biologically active agent from the supporting scaffold. Exemplary factors when considering a polymer-based scaffold can include, without limitation, molecular weight of polymers, chain length of copolymer components, and ratio of copolymer components. Porosity of scaffolding can also be formed and designed so as to control degradation rate of a scaffold and/or release rate of a biologically active agent from a scaffold.

Selection of the matrix material can be utilized to provide a primary control of release rate of a biologically active compound from the loaded scaffold. For instance, selection of a biodegradable material can be utilized to increase the rate of release and provide a release mechanism that can be limited to a large extent by matrix degradation rate and to a lesser extent by diffusion of the active compound from the bulk material. Alternatively, materials can be utilized such that active compound release rate is limited by only one of diffusion (e.g., a non-degradable matrix) or matrix degradation rate (e.g., essentially no diffusion of the active compound through the matrix due to small matrix mesh size).

In one embodiment, the implantable devices can be based upon particulate polymer matrices. In one embodiment, the particles can be nanosized and the average diameter of particles loaded with a biologically active agent can be about 1000 nanometers or less, about 200 nm or less, or about 100 nm or less in some embodiments. Alternatively, a device can utilize larger particulates, such as microparticles having a size of from about 1000 nanometers to about 50 micrometers (μm). Generally, particles are substantially spherical in shape, although other shapes including, but not limited to, plates, rods, bars, irregular shapes, etc., are suitable for use. Moreover, it should be understood that an implantable device is not limited to use of particulate-based scaffolds and larger scaffolds can alternatively be formed.

The preferred size and shape of the scaffolds can depend upon the specific application, e.g., the specific location and size of the adipose tissue in which the device will be implanted as well as the desired release rate of a biologically active agent from the scaffolds. For instance, in one embodiment, individual particles can be adhered to one another to form a larger, optionally porous bulk scaffold for implant. In another embodiment, particles can be of a size and shape so as to be injectable. As will be appreciated by those skilled in the art, the composition, shape, size, and/or density of the implantable devices may vary widely.

A biocompatible matrix can be loaded with one or more biologically active compounds according to any suitable method. For instance, in one exemplary embodiment illustrated in FIG. 1, a precipitation method can be utilized to form loaded particles in a one- or multi-step formation process. According to this method, a particle bulk material (e.g., a biocompatible polymer such as poly-(D,L-lactide-co-glycolide or a PGA/PLA copolymer or precursors thereof) can be dissolved in a solvent. Suitable solvents can depend upon the specific materials involved. For example, organic solvents including acetone, tetrahydrofuran, dimethylsulfoxide, dimethylformamide, or acetonitrile and the like can be utilized. This solution can undergo standard processing such as sonication, etc., so as to adequately solubilize the polymer. This solution can then be added, generally dropwise, to a second precipitating solution. The second solution can be, e.g., an aqueous solution. Either spontaneously or following an emulsification method, for instance following sonication, particles can form that include the polymer bulk material.

According to a single-step formation process, a biologically active agent (e.g., resveratrol) can also be included in either the first solution or the second solution. Upon formation of the particles, the agent can be incorporated within the polymer bulk material of the particles.

In another embodiment, a biologically active agent, e.g., a modulator or a precursor thereof, can be incorporated into a biocompatible matrix following matrix formation in a multi-step formation process, e.g., via dispersion optionally in conjunction with a driving force, e.g., sonication, high pressure, stirring, etc.

Figure 2:
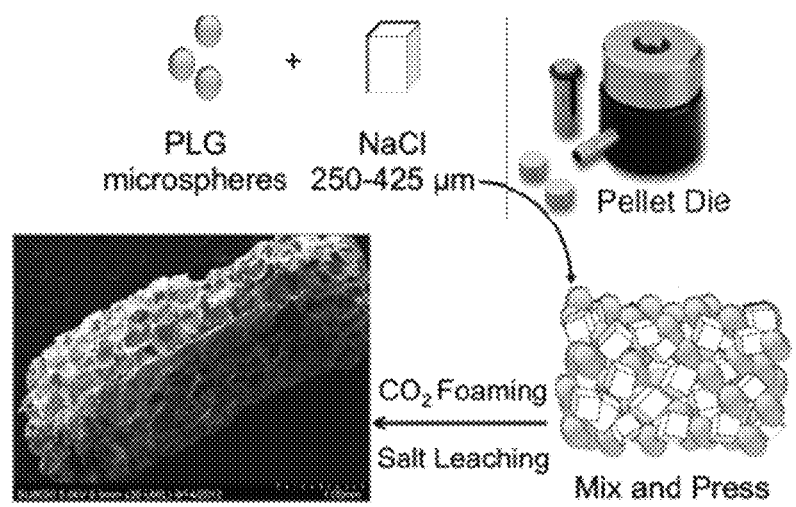
FIG. 2 schematically illustrates a scaffold fabrication technique as may be utilized in forming an implant.

Large implants can be formed in one embodiment through combination of a plurality of smaller particulate matrices. Porosity can be incorporated in an implant through utilization of a sacrificial material (e.g., NaCl) during formation of the scaffold. One embodiment for forming a porous scaffold according to this approach is schematically illustrated in FIG. 2. In addition, excellent control of the loading concentration can be attained through a particulate-based approach through utilization of blank particles (i.e., particles that do not include a modulator) in conjunction with the loaded particles. Of course, other scaffold formation approaches as are known in the art may be optionally employed to provide biocompatible scaffolds of any desired size, shape, and release profile.

Depending upon the particular characteristics of the biocompatible matrix and the biologically active agent(s), as well as the desired release profile, the biologically active agents can be simply encapsulated in a matrix or alternatively can be bonded to the matrix via either covalent or non-covalent bond formation. For instance, as described above with regard to lactic acid, in one embodiment a modulator can be provided as a component of a matrix that is released upon in vivo degradation or modification of the matrix. In another embodiment, a modulator (or a precursor thereof) can be bonded to the matrix as a pendant group to a polymer backbone and can be released from the matrix to provide desired activity following implantation. In yet another embodiment, a modulator can provide desired functionality while remaining bonded to the matrix, optionally following activation.

A biologically active agent can be provided in a biocompatible scaffold in a wide range of concentrations, generally depending upon the nature of the matrix, the active agents, and the desired release profile of the biologically active agent. In one embodiment, loading concentration of a biologically active agent in a matrix can vary from about 4 wt. % to about 40 wt. % or greater, by weight of the matrix, with higher and lower concentrations possible depending upon specific agent, matrix bulk material, and the like.

Implantable devices can include additional components as are generally known in the art including, without limitation, antibiotics, binding ligands, etc.

Loaded scaffolds can be formed and implanted so as to control the rate of release of a modulator or precursor thereof from a matrix. Suitable control mechanisms are known to those of skill in the art. For instance, release rates can depend upon the relative concentration of active compound to bulk material, upon the molecular weight and degradation characteristics of the bulk material, upon the mesh size of a polymer matrix, upon the presence or strength of a binding mechanism between the matrix and an active compound, and so forth, as is known. In any of these cases, one of ordinary skill in the art is capable of engineering a system so to achieve desirable release rate. For instance, in the case of purely diffusion-limited release, such control can be achieved by variation of compound concentration within a scaffold and/or scaffold size, polymer mesh size, and so forth. In the case of purely degradation-limited release, polymer monomer units, for instance glycolic acid content of a PLG polymer, and/or molecular weight of particle bulk material, as well as particle size, can be adjusted to "fine tune" active compound release rate. For example, use of PLG polymers with higher glycolic acid content and lower molecular weight can lead to an increased degradation rate of a matrix formed with the polymer. Release rate of active compound from scaffolds can be adjusted utilizing such parameters so as to produce carriers capable of sustained release for periods varying from a few days to a few months, with the maximum release rates generally varying from a few hours to a few weeks.

During use, the devices can be implanted in any type of adipose tissue in conjunction with any type and combination of cell types. For instance, a device can be implanted in either white adipose tissue or brown adipose tissue. In addition, a device can be implanted in visceral fat, subcutaneous fat, or intramuscular fat. In one embodiment, a device can be implanted directly in central (abdominal) adipose tissue, for instance in treatment of obesity.

As described in more detail below, scaffold-based delivery of a modulator or a precursor thereof directly to adipose tissue can prevent weight gain in mice fed a 60% high fat diet. Interestingly, mice implanted with the agent-containing scaffolds consumed less food compared to control mice, suggesting the devices can preserve or promote leptin signaling between the adipose and hypothalamus. As described, glucose intolerant mice that received implanted devices demonstrated enhanced glucose sensitivity during an intraperitoneal glucose tolerance test as compared to insulin resistant mice that received sham surgery or blank scaffolds. Without wishing to be bound to any particular theory, it is believed that the efficacy of disclosed devices may be supported by direct delivery of a modulator (or precursor thereof) to the fat tissue. Oral delivery generally cannot achieve such success because active agents are often eliminated from the body without successful targeting to the adipose, and systemic delivery calls for a much larger dosage, with a much higher likelihood of unsuccessful delivery and undesirable side effects. For instance, therapeutic efficacy of resveratrol when administered orally in animal models requires a dose between 40 and 400 mg/kg/day. By use of disclosed devices, a modulator can be provided directly to the adipose tissue in a depot containing 20 mg/kg—thus the rate of delivery can be 20 mg/kg/day or less when utilizing a sustained delivery of active agent.

The present disclosure may be better understood with reference to the Examples set forth below.

EXAMPLES

Blank Scaffold Fabrication

Figure 3:
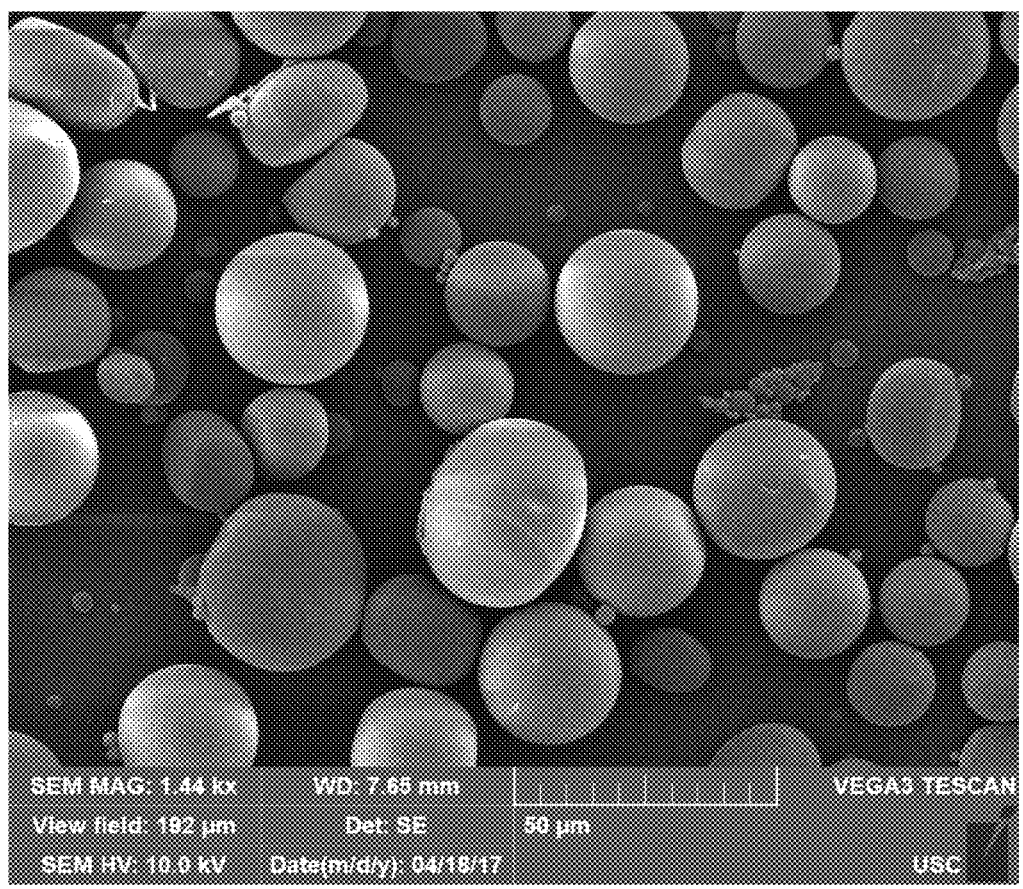
FIG. 3 is a scanning electron microscope (SEM) image of particulate scaffolds as may be formed in one embodiment.

Poly(lactide-co-glycolide) (PLG) microspheres were prepared as schematically illustrated in FIG. 2. Briefly, PLG (75:25 mol ratio d,l-lactide to glycolide, 0.76 dL/g) (Evonik) was dissolved in dichloromethane to make a 6% (w/w) solution, which was then emulsified in 1% poly(vinyl alcohol) to create microspheres. The microspheres were collected by centrifugation, washed with deionized water, and lyophilized overnight. FIG. 3 is an SEM showing typical microspheres.

Figure 4:
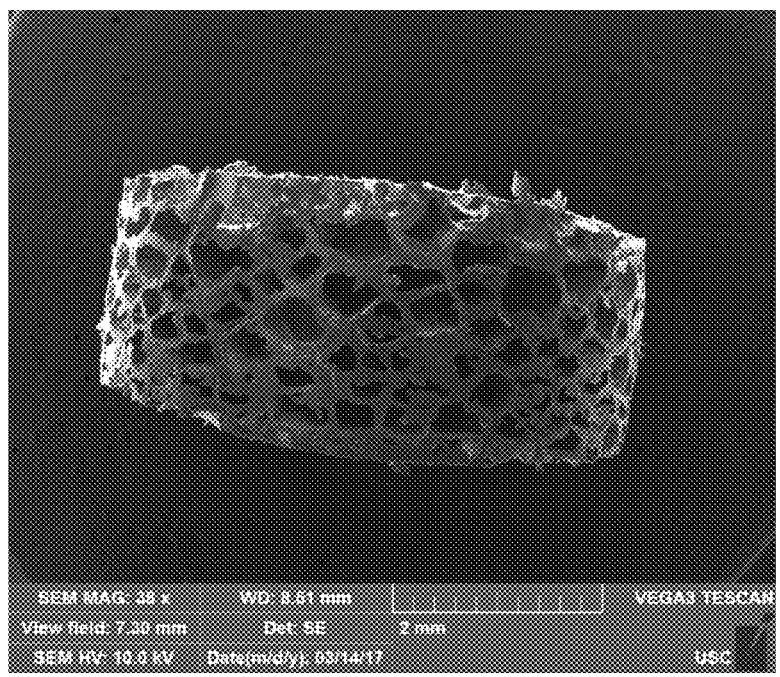
FIG. 4 is a side view of a porous scaffold.
Figure 5:
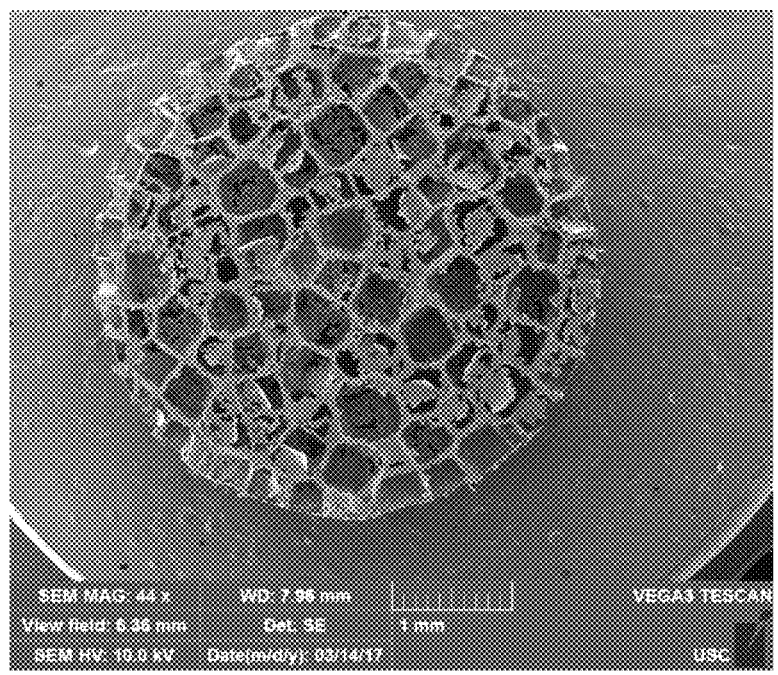
FIG. 5 is a top view of a porous scaffold.
Figure 6:
FIG. 6 is a photograph of a scaffold adjacent a coin for size reference.

Microspheres were combined in a 1:30 ratio with NaCl particles 250-500 μm in diameter. The mixture was pressed in a steel die at 1000 pounds per square inch (psi) and gas-foamed after equilibration to 800 psi under $CO_2$ gas. Salt particles were removed by immersion in deionized water with repeated washing. Prior to implantation, scaffolds were sterilized in 70% ethanol and then washed twice in sterile phosphate buffered saline (PBS; Life Technologies). FIG. 4 and FIG. 5 provide a side and top view, respectively, of formed scaffolds. FIG. 6 illustrates a scaffold adjacent a coin for reference. The scaffold is approximately 5 mm in diameter and approximately 1.5 mm in height. The volume of the scaffold would be about ¼ of the volume of a fat pad from a typical obese mouse.

Animals

Male C57BL6/J mice were purchased from Jackson Laboratory at 6 weeks of age. All animals were housed with ad libitum access to water and food in a temperature-controlled room with a 12:12 h light:dark cycle under specific pathogen-free conditions. All procedures were performed in accordance with NIH Guidelines for Care and Use of Animals and were approved by the Institutional Animal Care and Use Committee at the University of South Carolina. Two weeks after arrival the mice were placed on a high fat diet (Research Diets D12492). On caloric basis, the high-fat diet consisted of 60% fat from lard, 20% carbohydrate, and 20% protein (total 5.24 kcal/g). Mice were kept on the high fat diet for one week prior to scaffold implantation and remained on the diet for the remainder of the experiment.

Scaffold Implantation

Mice received bilateral implants of two scaffolds in the epididymal fat. Briefly, mice were anesthetized with a 2% mixture of isoflurane and oxygen (2 L/min), and the abdominal midline was shaved and prepped in a sterile fashion. Following a lower abdominal midline incision, scaffolds were wrapped in both the left and right epididymal fat and returned to the intraperitoneal cavity. The abdominal wall was then closed with a running stitch, and the skin was closed with wound clips.

Duel-Energy X-Ray Absorptiometry

Body composition was assessed in all mice using DEXA scan (Lunar PIXImus) two days before surgery and two weeks post-surgery. Each mouse was anesthetized for the duration of the procedure (5 min) by exposure to 1-2% isoflurane-oxygen gas via nose cone. Each mouse was placed on the scanner bed in the prone position, with the limbs and tail stretched away from the body. One scan per mouse was performed and analyzed with PIXImus software (Lunar). The head was excluded from calculation using a manual ROI. The PIXImus was calibrated with an aluminium/lucite phantom (corresponding to bone mineral density=0.0592 $g/cm^2$ and 12.5% fat) on each day of testing according to the manufacturer's instructions.

Intraperitoneal Glucose Tolerance Test

For intraperitoneal glucose tolerance tests (IPGTT), mice were fasted for 6-hours before receiving injections of D-glucose into the intraperitoneal cavity. Glucose administered was normalized to the lean mass calculated via a DEXA scan that was conducted one-day prior (2 g glucose per kg lean mass). Blood samples were collected via a tail vein prick at 0, 15, 30, 60, 90, and 120 minutes after glucose administration. Glucose measurements were obtained using a handheld glucose meter (Accu-Chek Nano and Smartview test strips).

Resveratrol Encapsulation within PLG Microspheres

Poly(lactide-co-glycolide) (75:25 mol ratio lactide to glycolide) (Lakeshore Biomaterials) was dissolved in dichloromethane to make an 8% (w/w) solution. Resveratrol (Sigma) was solubilized in 200 proof ethanol (Sigma) to make a 5% w/w solution. The two solutions were then combined in a 3:1 ratio of PLG in dichloromethane to resveratrol in ethanol and mixed together to form a homogenous solution. The PLG-Resveratrol solution was placed in an aqueous solution containing a surfactant (1% PVA) and homogenized at 7000 rpm resulting in the formation of microspheres through single emulsion. The ethanol and dichloromethane was allowed to evaporate off and the microspheres were collected by centrifugation. After collection, microspheres were suspended in deionized water, frozen, and lyophilized for 48 hours.

Resveratrol Loaded Scaffold Fabrication

Scaffolds were fabricated using a gas foaming salt leaching technique. PLG microspheres were combined with NaCl particles ranging from 250-500 μm in diameter in a 1:30 ratio and pressed under 1 ton of pressure into cylinders 5 mm in diameter and 2 mm in height. Scaffolds were then gas-foamed after equilibration to 800 psi under $CO_2$ gas in a custom-made pressure vessel. Salt particles were removed from the foamed scaffolds by immersion in 50 mL deionized water for 1 hour. In order to control the amount resveratrol contained within the scaffolds, resveratrol encapsulated PLG microspheres were combined with blank PLG microspheres in ratios of 50:50 (50% resveratrol Scaffolds), 10:90 (10% resveratrol scaffolds as well as pure resveratrol microspheres (100% resveratrol scaffolds) and pure blank particles (0% resveratrol scaffolds). These ratios of microspheres were then mixed with NaCl and fabricated as described above.

Quantification of Resveratrol within Resveratrol Loaded PLG Scaffolds

Scaffolds containing resveratrol were each dissolved in 1 mL of dimethyl sulfoxide (DMSO) and compared against an 8-point standard curve made by making ½ dilutions of a 1000 μg/mL solution of resveratrol (Sigma) in DMSO containing identical concentrations of PLG as the scaffold solutions. All samples were loaded into a UV-Star® 96 well plate (Greiner Bio-One) and scanned for absorption at 330 nm in a Biotek Synergy 2 plate reader.

Encapsulation Study

Figure 7:
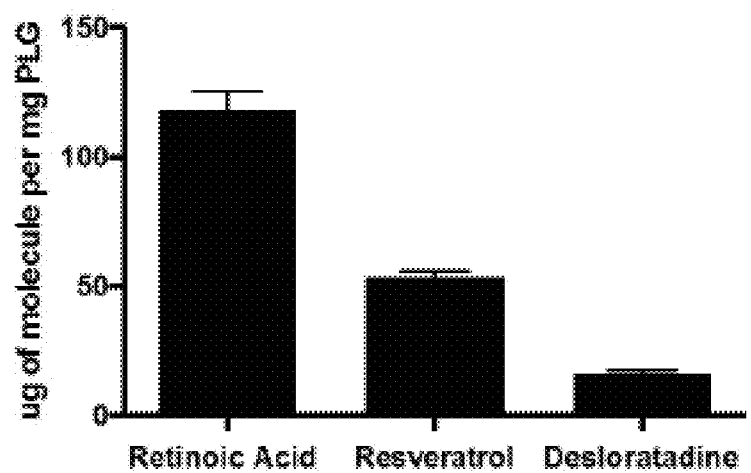
FIG. 7 illustrates the successful loading of trans-retinoic acid, resveratrol, or desloratadine into polymer scaffolds and compares the loading quantities for each.
Figure 8:
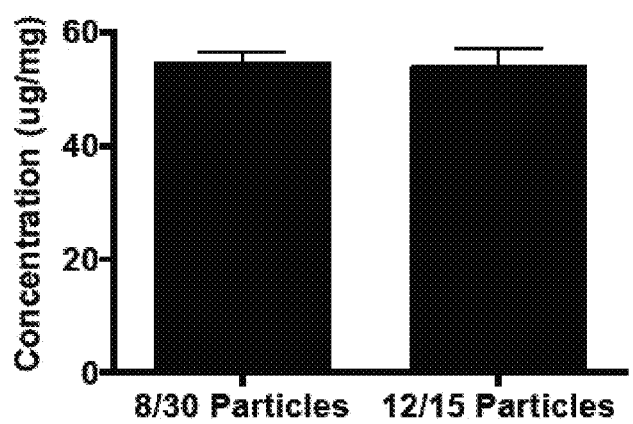
FIG. 8 compares the results for two syntheses forming resveratrol-encapsulated poly(lactide-co-glycolide) (PLG) microspheres demonstrating process reproducibility.
Figure 9:
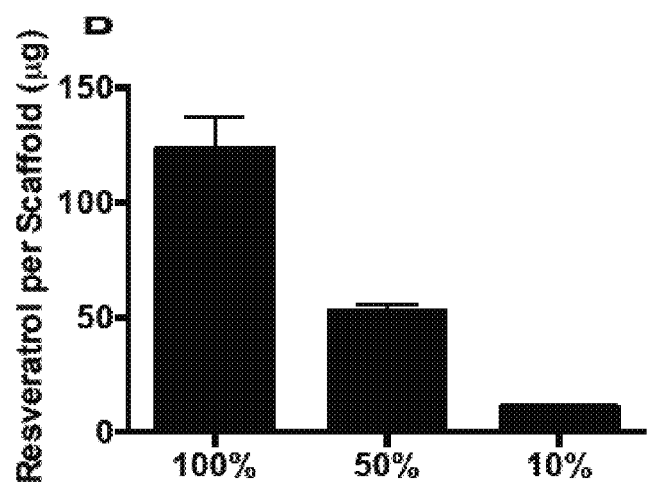
FIG. 9 illustrates the successful controlled loading of resveratrol into polymer scaffolds through determination of mass resveratrol per mass of scaffold when 100%, 50%, or 10% of the polymer particles contain resveratrol.
Figure 10:
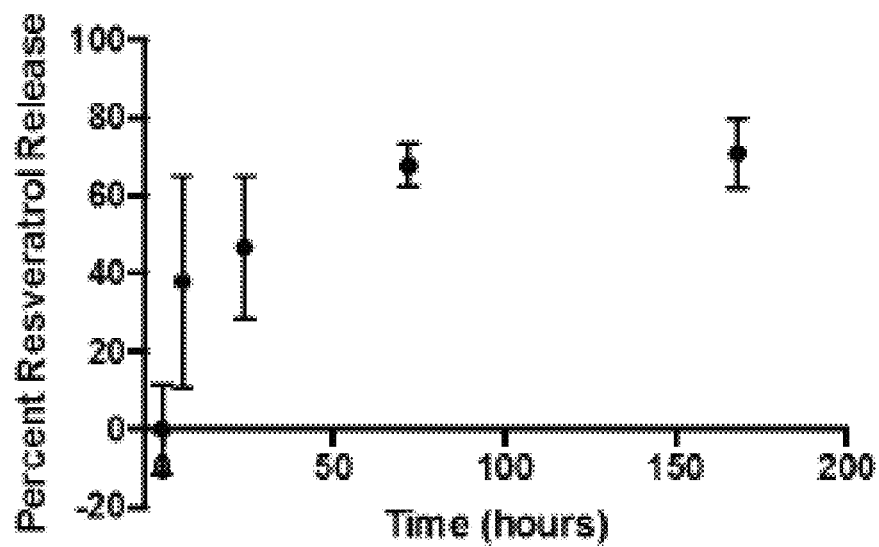
FIG. 10 presents an in vitro release profile for resveratrol from loaded PLG-based scaffolds.

PLG scaffolds were formed as described above containing one of trans-retinoic acid, resveratrol, or desloratidine encapsulate therein. Quantification of components encapsulated within PLG scaffolds is shown in FIG. 7. FIG. 8 presents a comparison of resveratrol encapsulation between two syntheses of resveratrol encapsulated PLG microspheres, demonstrating process reproducibility. Quantification of resveratrol within scaffolds made with 10%, 50%, and 100% resveratrol microspheres is presented in FIG. 9, and FIG. 10 presents an in vitro release profile for resveratrol from loaded PLG scaffolds.

Integration Study

Figure 11:
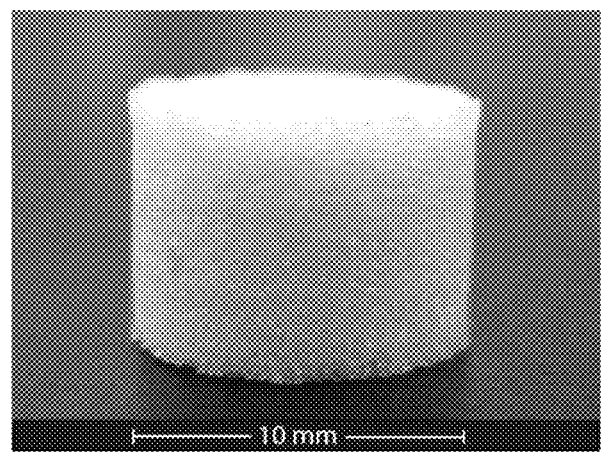
FIG. 11 illustrates a scaffold utilized in examples described herein.
Figure 12:
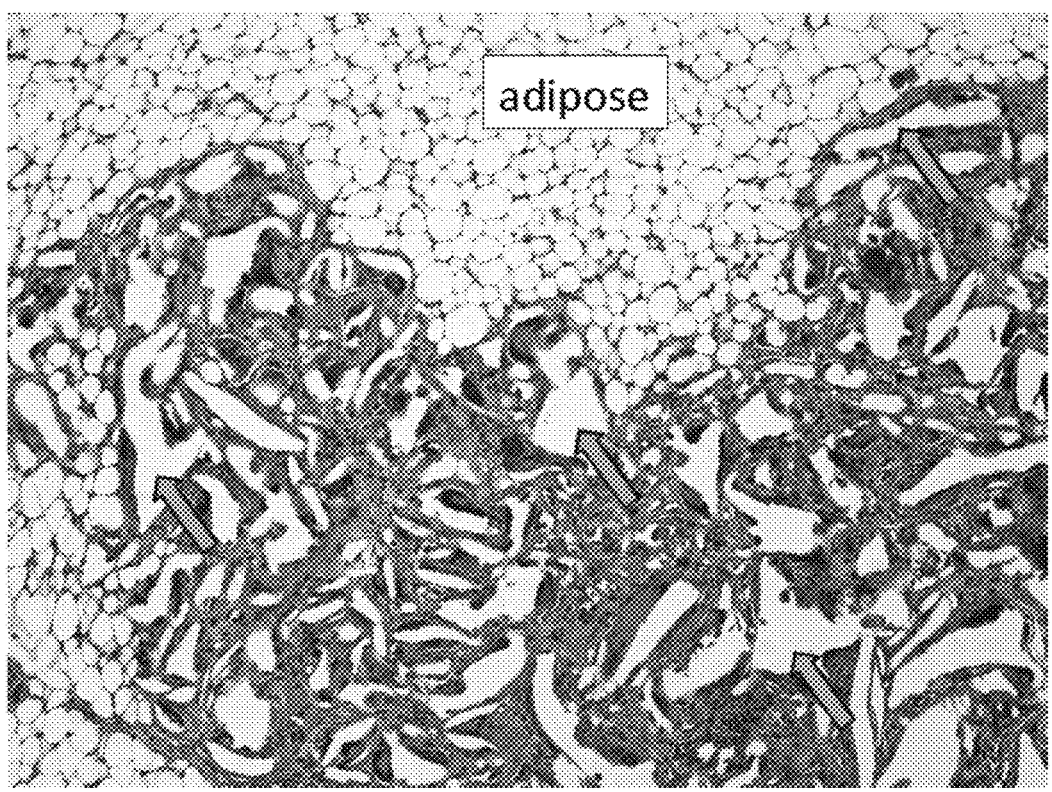
FIG. 12 illustrates Haemotoxylin and Eosin (H&E) staining of adipose tissue 28 days following implant with the scaffold of FIG. 11.

Blank PLG scaffolds (no active agent loaded therein) were formed and implanted into the adipose tissue of five-week old, male C57Bl/6 mice. FIG. 11 includes an image of a scaffold prior to implant and FIG. 12 illustrates H&E staining of the adipose tissue 28 days following the implant. The arrows indicate polymer matrix in contact with adipocytes. The staining results indicate that there is cellular infiltration and matrix deposition within the polymer scaffold.

Leptin Study

Figure 13:
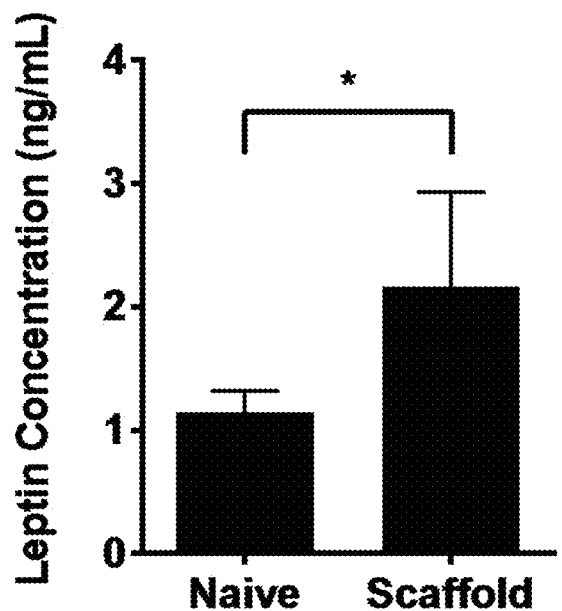
FIG. 13 compares the plasma leptin concentration of mice implanted with resveratrol-containing scaffolds with control mice.

Five-week old, male C57Bl/6 mice received scaffold implants formed as described above containing resveratrol into each epididymal fat pad (two scaffolds per mouse). 14 days later blood was harvested from the mice and compared to blood harvested from mice that did not receive any implant. The plasma was analyzed via ELISA. Results are shown in FIG. 13. (*Indicates P<0.05 versus sham and blank as determined by 2-way ANOVA with Tukey posttest. Error bars indicate standard deviation.)

Prevention Study

Five-week old, male C57Bl/6 mice received scaffold implants formed as described above into each epididymal fat pad (two scaffolds per mouse). Scaffolds were either blank or contained 100 µg of resveratrol (200 µg per mouse). "Sham" examples were subjected to the surgical procedure, but no implant was placed in the mice. (Five mice per group.) Twenty-eight days post-implant, following a time when the scaffolds were integrated within the adipose tissue, the mice were fed a 60% high fat diet (Research Diets 12492).

Figure 14:
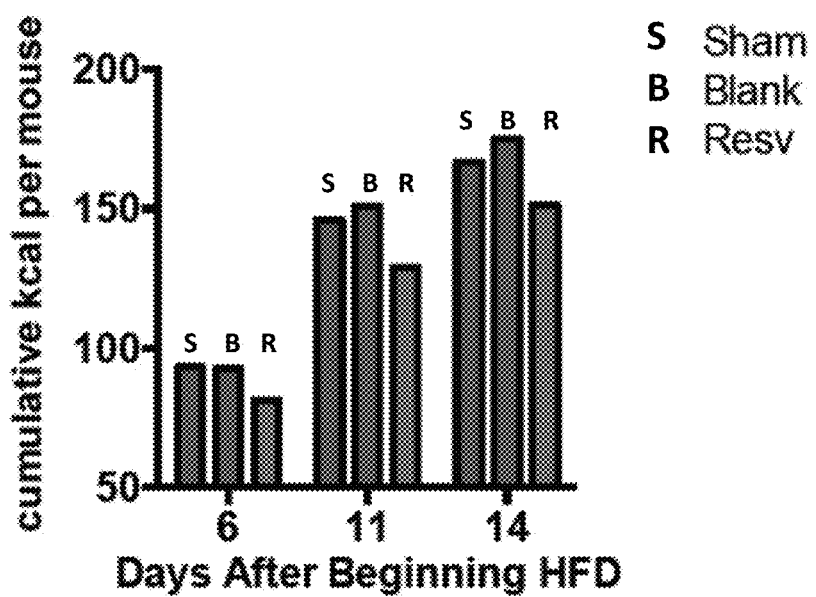
FIG. 14 presents the cumulative kilocalories (kcal) consumed per mouse at 6, 11, and 14 days after beginning the high fat diet.
Figure 15:
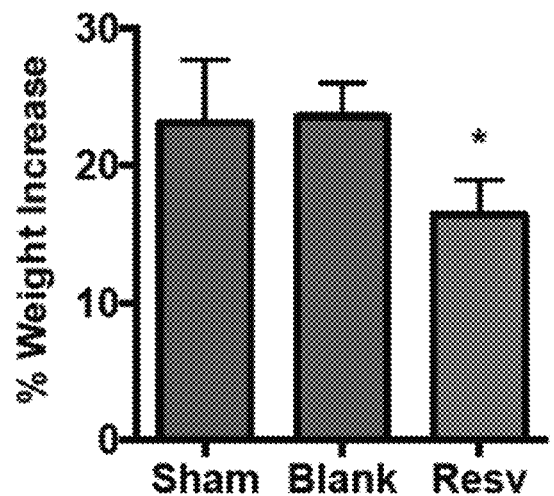
FIG. 15 presents the percent increase in weight per group after 14 days of the high fat diet.

As shown in FIG. 14 and FIG. 15, mice implanted with resveratrol-containing scaffolds ate less food (FIG. 14) and gained significantly less weight (FIG. 15) as compared to mice receiving blank scaffolds or sham surgery. (*Indicates P<0.05 versus sham and blank as determined by 2-way ANOVA with Tukey posttest. Error bars indicate standard deviation.)

Reversal Study

Figure 16:
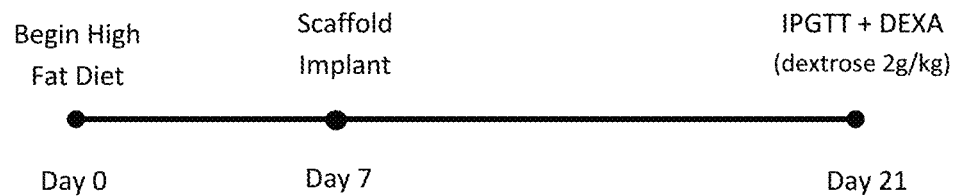
FIG. 16 presents a timeline of an experiment in which mice were fed a high fat diet and following were implanted with resveratrol-containing scaffolds.

In another test, mice were fed a high fat diet and monitored for glucose tolerance using an intraperitoneal glucose tolerance test (IPGTT). The timeline for the study is shown in FIG. 16. At day 7, mice received scaffold implants either containing 100 µg resveratrol (two implants per mouse) or blank implants, or were subjected to a sham surgery. Two weeks after surgery (3 weeks of high fat diet) an IPGTT and DEXA were conducted.

Figure 17:
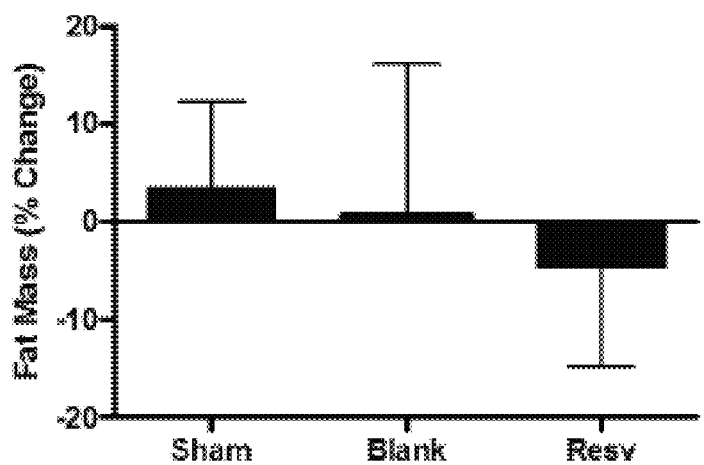
FIG. 17 presents a comparison of fat mass from pre-surgery to fat mass two weeks post-surgery for the experiment of FIG. 16.
Figure 18:
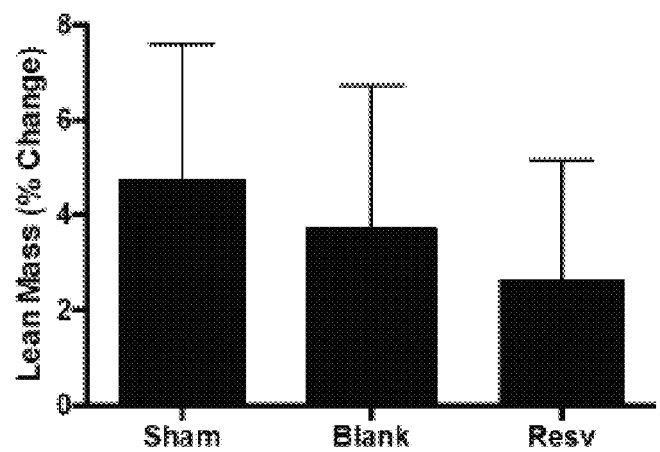
FIG. 18 presents a comparison of lean mass from pre-surgery to lean mass two weeks post-surgery for the experiment of FIG. 16.
Figure 19:
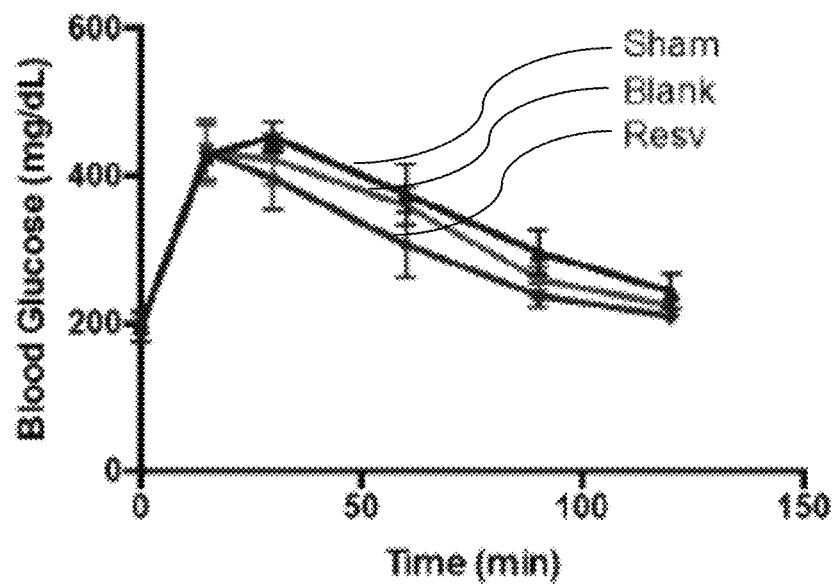
FIG. 19 presents the blood glucose measurements from an intraperitoneal glucose tolerance test completed 2 weeks post-surgery for the experiment of FIG. 16.
Figure 20:
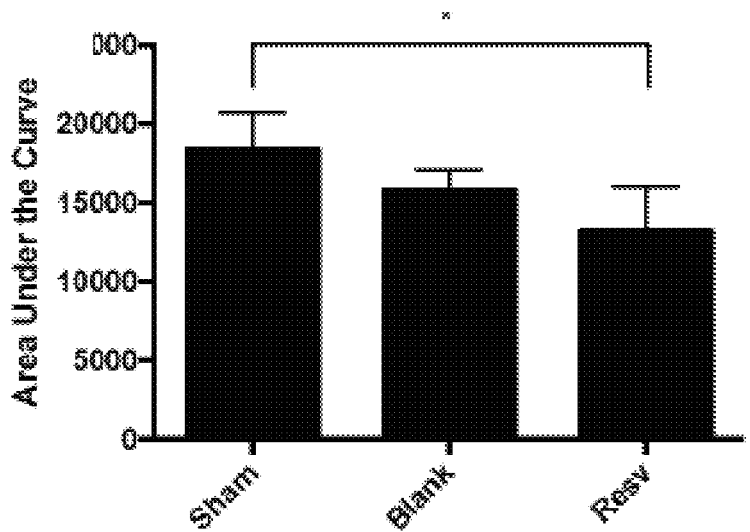
FIG. 20 presents the area under the curve of FIG. 19 for mice of the different groups (sham, blank, or resveratrol).

FIG. 17 presents a comparison of fat mass from pre-surgery to fat mass two weeks post-surgery. FIG. 18 presents a comparison of lean mass from pre-surgery to fat mass two weeks post-surgery. No significant differences are noted. As shown in FIG. 19 and FIG. 20, mice receiving resveratrol scaffold implants had significantly lower blood glucose measurements at 30 and 60 minutes post dextrose injection compared to mice that received sham surgery or blank implants (data obtained two weeks post-surgery).

FIG. 17 demonstrates after three weeks of the high fat diet, mice that received the resveratrol-containing scaffolds exhibited a 5% decrease in body fat, while sham mice showed a 5% increase in body fat as measured by dual-energy X-ray absorptiometry (DEXA). The overall data indicate that scaffold-based resveratrol delivery to the visceral adipose tissue can both protect and prevent against metabolic disorder induced by a 60% high fat diet.

Figure 21:
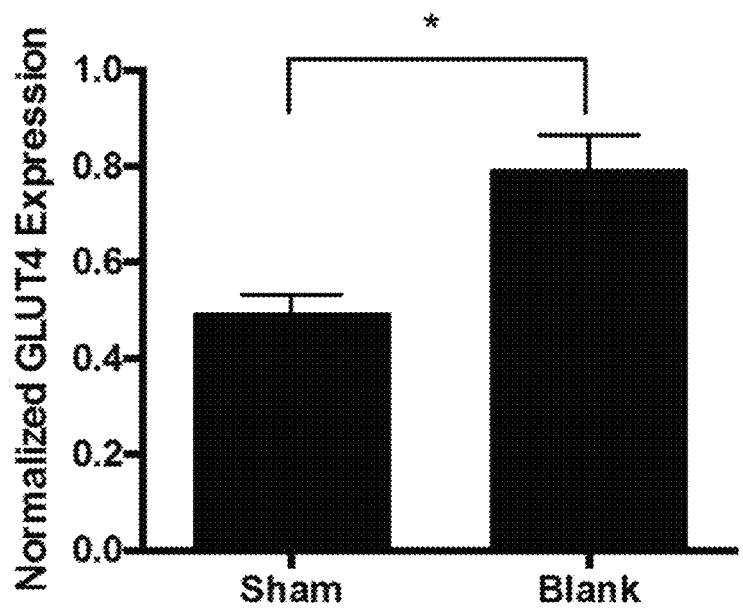
FIG. 21 compares the normalized GLUT4 expression in the gastrocnemius muscle of mice implanted with scaffold and control mice.

To address how the implanted scaffolds were functioning, gastrocnemius muscle was collected fourteen days after scaffold implant into the adipose tissue (twenty-one days after beginning the high fat diet). Western blot analysis indicated that glucose transporter type 4 (GLUT-4) was elevated (60% higher) in the muscle of mice receiving blank scaffold implants compared to controls (FIG. 21), which was consistent with the enhanced glucose clearance from the blood stream measured during the IPGTT. Interestingly, mice with blank scaffolds expressed approximately the same about of GLUT4 in the calf muscle as healthy age-matched mice that had been on chow their entire lives.

Figure 22:
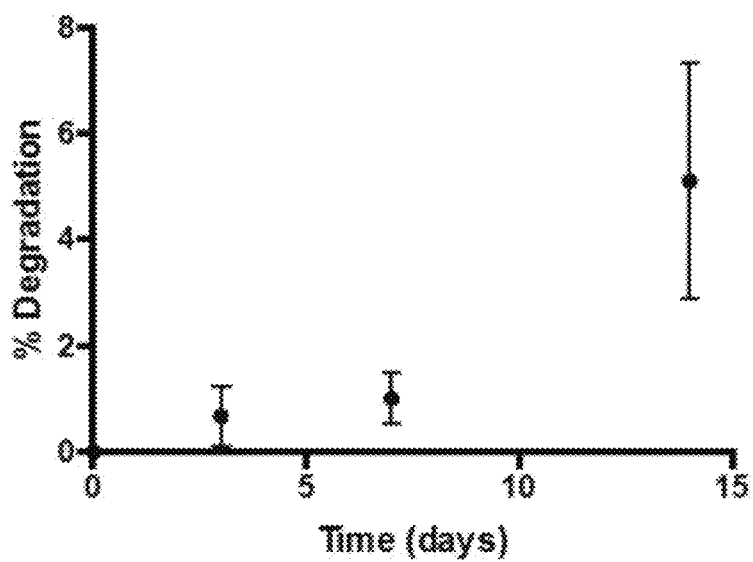
FIG. 22 presents the 14 day degradation profile of implanted scaffolds.

FIG. 22 presents the degradation profile of scaffolds over 14 days.

Figure 23:
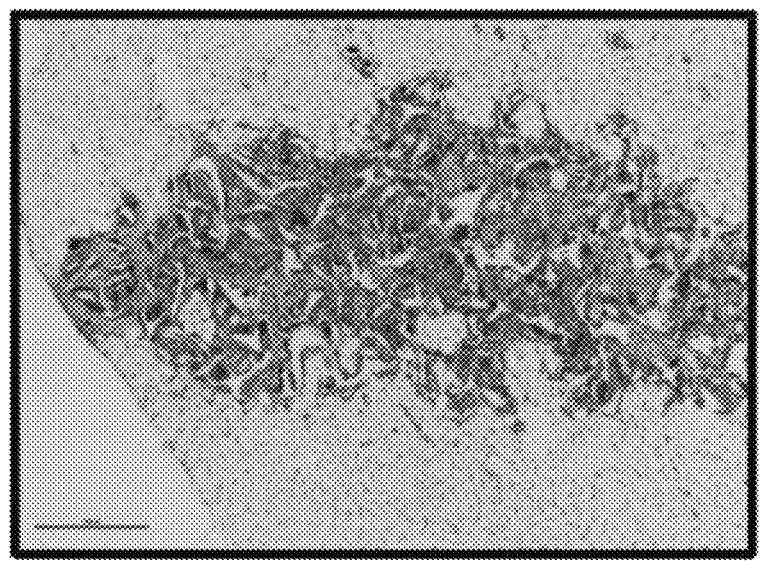
FIG. 23 illustrates H&E staining of tissues adjacent a blank scaffold 14 days after implant into the epididymal fat.
Figure 24:
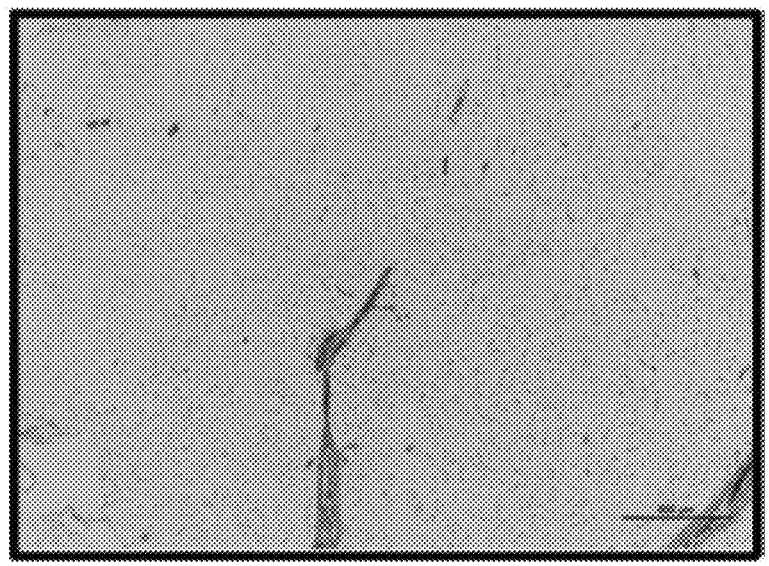
FIG. 24 illustrates H&E staining of an epididymal fat pad from a mouse receiving a sham surgery.
Figure 25:
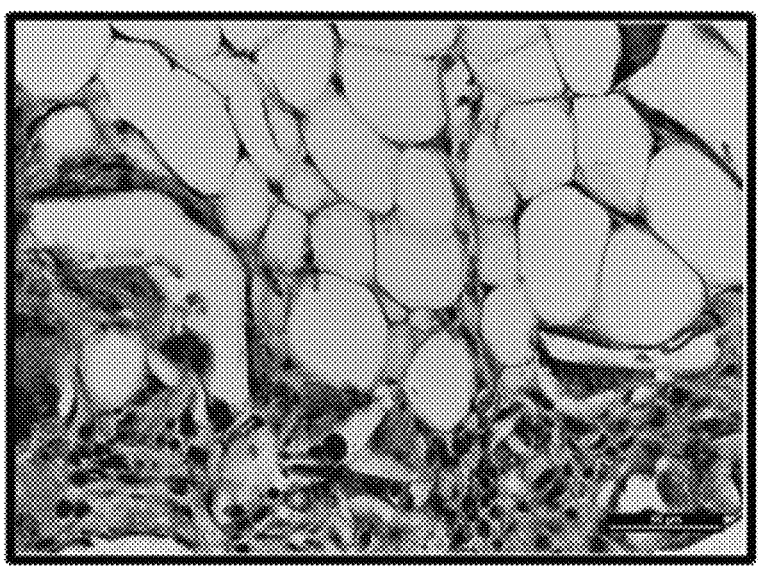
FIG. 25 is a 40× magnification of the blank scaffold-adipose interface of FIG. 23.
Figure 26:
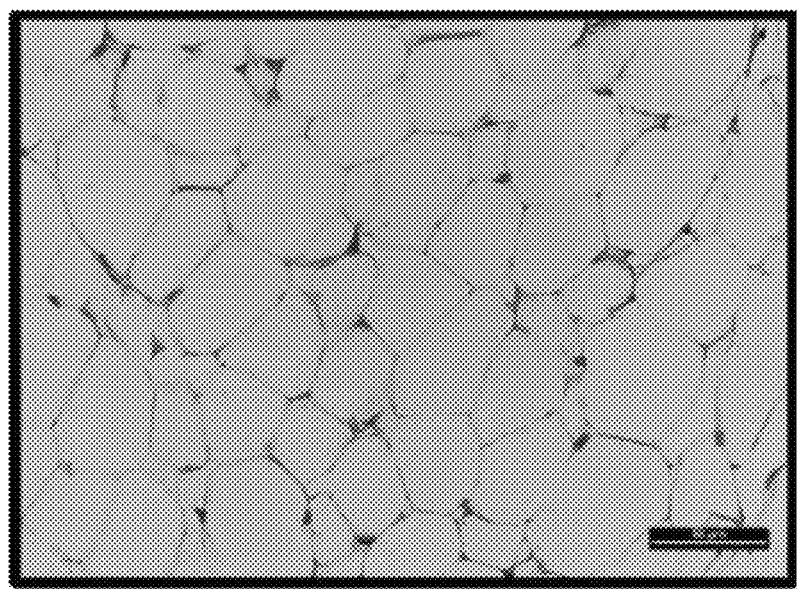
FIG. 26 is a 40× magnification of sham surgery fat pad of FIG. 24.

FIG. 23 illustrates hematoxylin and eosin staining of tissues adjacent a blank scaffold implanted into the epididymal fat pad. FIG. 24 illustrates hematoxylin and eosin staining of an epididymal fat pad from a mouse receiving a sham surgery. FIG. 25 is a 40× magnification of the blank scaffold-adipose interface and FIG. 26 is a 40× magnification of sham surgery fat pad. All images were taken fourteen days post-implant.

Figure 27:
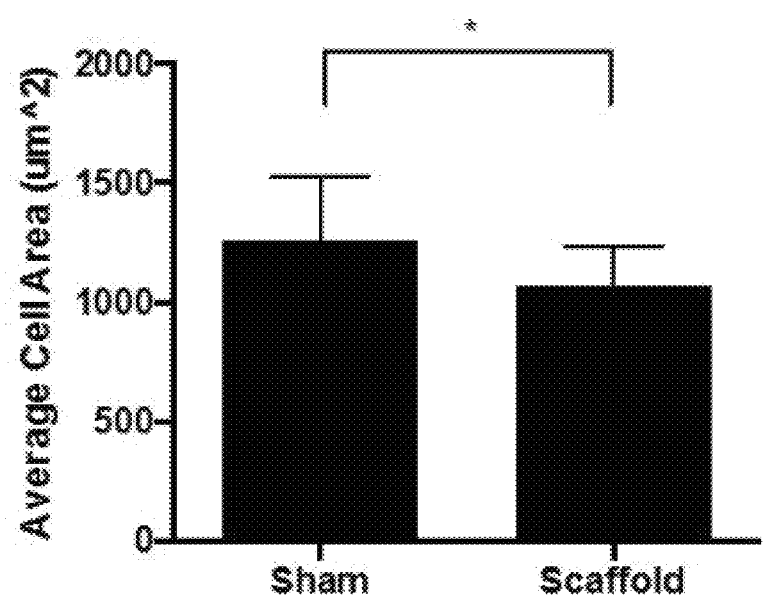
FIG. 27 presents a quantification of average adipocyte area in epididymal fat pads receiving sham and blank scaffold implants in healthy chow-fed mice.
Figure 28:
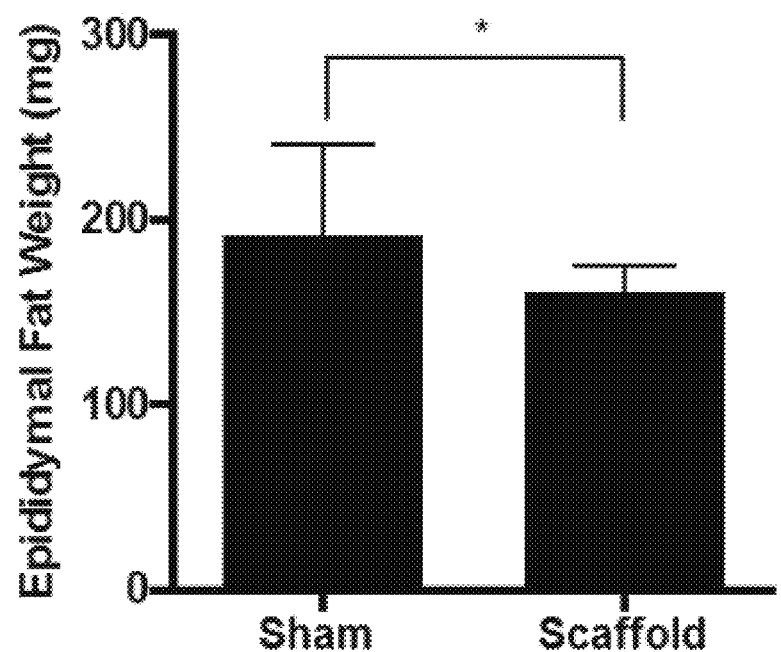
FIG. 28 compares the average weight of epididymal fat pads between mice receiving the sham surgery and those receiving the blank scaffolds.

FIG. 27 presents a quantification of average adipocyte area in epididymal fat pads 14 days after receiving either sham or blank scaffold implants in health chow-fed mice. FIG. 28 compares the average weight of epididymal fat pads between the mice receiving the sham surgery and those receiving the blank scaffolds.

While certain embodiments of the disclosed subject matter have been described using specific terms, such description is for illustrative purposes only, and it is to be understood that changes and variations may be made without departing from the spirit or scope of the subject matter.

What is claimed is:

1. A method for treating a metabolic disorder comprising implanting a biocompatible structure in adipose tissue, the biocompatible structure comprising a biocompatible matrix and resveratrol (3,5,4'-trihydroxy-trans-stilbene), the biocompatible matrix comprising a poly(lactic-co-glycolide) copolymer, the biocompatible structure being configured to release the resveratrol into the adipose tissue over time.

2. The method of claim 1, wherein the biocompatible matrix is biodegradable.

3. The method of claim 1, the resveratrol directly or indirectly modifying one or more of cell growth and/or differentiation, catecholamine responsiveness, triglyceride synthesis, lipase activity, differentiation-specific gene expression, lipid metabolism, fatty acid uptake, and accumulation of cytoplasmic lipid.

4. The method of claim 1, wherein the adipose tissue expression product modulator modifies the expression of a sirtuin.

5. The method of claim 1, wherein the adipose tissue comprises visceral adipose tissue.

* * * * *